United States Patent [19]

Kipp

[11] 4,380,436
[45] Apr. 19, 1983

[54] SUPPORT FOR A REMOVABLE DENTAL PROSTHESIS

[75] Inventor: Manfred Kipp, Sande, Fed. Rep. of Germany

[73] Assignee: Dental Keramik Sande GmbH, Sande, Fed. Rep. of Germany

[21] Appl. No.: 307,392

[22] Filed: Oct. 1, 1981

[30] Foreign Application Priority Data

Feb. 28, 1980 [DE] Fed. Rep. of Germany ....... 3107690

[51] Int. Cl.³ ............................................. A61C 13/22
[52] U.S. Cl. .................................................. 433/182
[58] Field of Search ............... 433/172, 181, 182, 183

[56] References Cited

U.S. PATENT DOCUMENTS 1,693,845 12/1928 Kellner et al. ...................... 433/182
1,705,504 3/1929 Sorensen ............................ 433/181

FOREIGN PATENT DOCUMENTS 791336 12/1935 France ................................. 433/180

Primary Examiner—Robert Peshock
Attorney, Agent, or Firm—Allison C. Collard; Thomas M. Galgano

[57] ABSTRACT

The invention relates to a support for retaining a removable dental prosthesis on the remainder of one's natural teeth. In accordance with the invention, a conical pin is mounted on the crown base of a capped tooth. A slotted conical bushing is mounted on a dental prosthesis which bushing is received in a telescopic manner on the pin. The pin and the bushing are so disposed that they are positioned vertically between the capped tooth of the remainder of the natural teeth and the adjacent tooth of the dental prosthesis. The bushing is provided with a spring element which yieldingly engages into recesses of the pin when the bushing and the pin are in total engagement with each other, thus retaining the dental prosthesis in its end position. By a corresponding force application, the yielding snap connection can be easily released, so as to remove the dental prosthesis.

2 Claims, 1 Drawing Figure

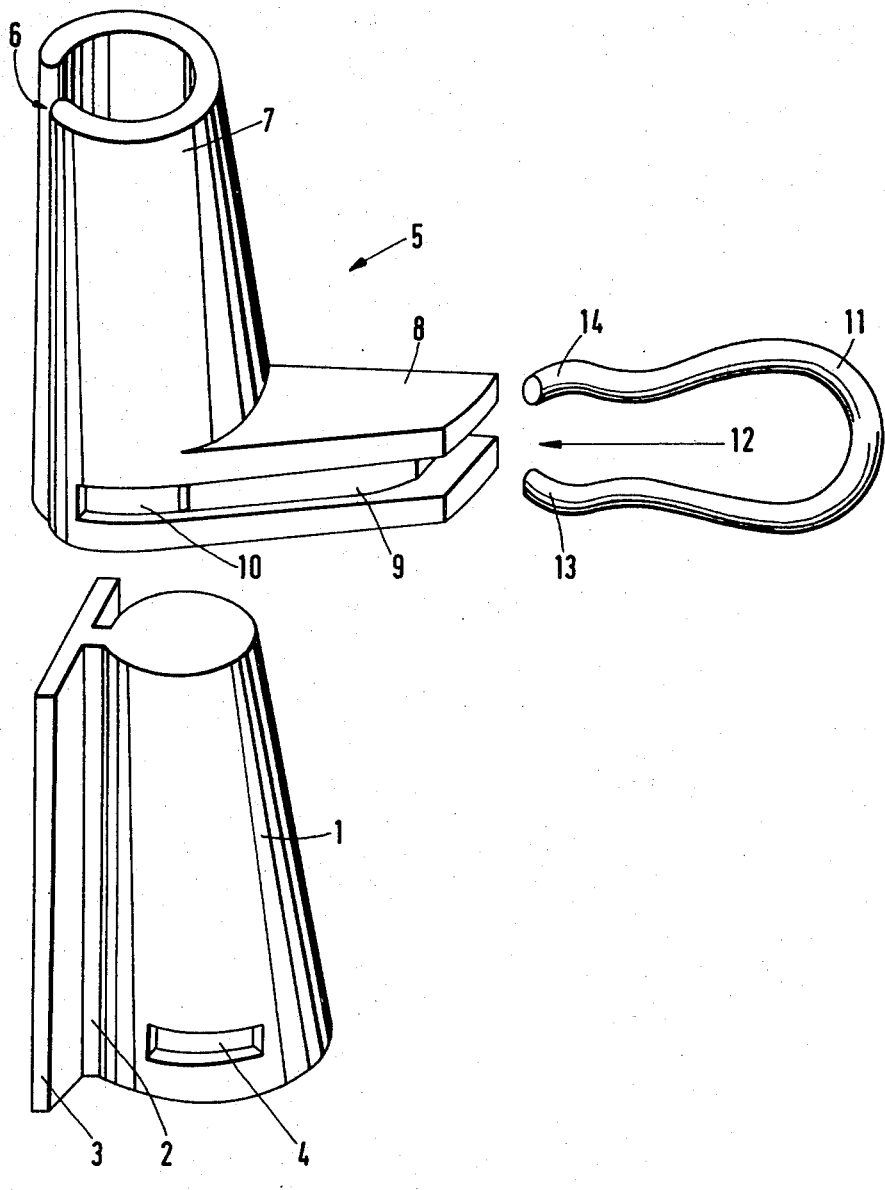

SUPPORT FOR A REMOVABLE DENTAL PROSTHESIS

The invention relates to a support for retaining a removable dental prosthesis on the remainder of one's natural teeth.

It is already known to provide a denture with supports which can be connected with the remainder of the natural teeth. Yokes or clamps can retain the denture on one or a plurality of the remainder of the natural teeth. Such supports have the basic advantage that the denture can be removed and placed back again. However, these known supports have the disadvantage that wear occurs during frequent usage, so that the seat of the denture becomes wobbly and unsafe.

It is therefore an object of the invention to improve such a support for a denture.

This object of the invention is attained by the provision of positively-locking and telescopically displaceable, as well as in the end position, mutually-engaging, support elements provided between adjacent teeth of a dental prosthesis and the remainder of the natural teeth. One of these support elements is a male support element preferably provided on the crown base of a capped tooth of the remaining natural teeth, and the other support element is a female support element preferably provided on the dental prosthesis.

The inventive support is characterized by a permanent solid seat of the dental prosthesis which, in particular, is obtained by the positive locking of the telescopically-displaceable support elements. An unintentional release of the support elements is prevented by the telescopic engagement. The mounting of a male support element on the crown base of a capped tooth of the remainder of the natural teeth is particularly solid and permanent with respect to hitherto known supports. It can be premade from metal, for example, gold or palladium and may previously be soldered onto the base of the crown while making the crown. It is also possible to make this part from residue-free combustible plastic material which can be mounted while shaping the crown and can be cast therewith. The capped tooth is then provided with the male support element for the remainder of the natural teeth.

The part which is the female member of the support element can be molded together with the dental prosthesis, and tooth parts can interengage in a positive locking manner, so that a safe mounting of the dental prosthesis is provided.

In a particular advantageous embodiment of the support, the support element which serves as the male support element is a vertically-disposed conical pin, and the support element which serves as the female support element is a vertically-extending conical bushing which is configured to encompass the pin. The conical shape of the male and female support elements facilitates the insertion or mounting of the dental prosthesis until final fixing or locking in place. Simultaneously, the conical design of the two parts of the supports provides the desired advantageous positive locking. Furthermore, the shape of the support in the form of a pin and bushing is advantageous in that forces which are exerted on the dental prosthesis and thereby on the support are distributed over a relatively large face, whereby material deformation of the support and material wear are reduced or avoided.

For releasable locking the interengaging support elements together, the conical bushing is preferably provided with an inwardly protruding spring element which engages a recess of the pin when the bushing is received on or encompasses the pin.

Advantageously, the spring element is a spring wire yoke which engages the exterior surface of the bushing and which has resilient segments which project into wall openings of the bushing and engages in groove-like recesses of the pin when the bushing is in its final end position when pushed over the pin.

The use of a wire spring yoke which engages the exterior surface of the bushing is advantageous in that it affords a relatively easy replacing of the spring element, if the spring effect becomes weak or if any other mechanical damage thereto occurs which would impair the engagement of the interengaging support elements. This is because the spring element is accessible to corresponding tools when the dental prosthesis is removed.

One embodiment of the invention showing further inventive features is shown in the drawing.

In the drawing, a schematic, perspective view of the individual elements of a support embodying the present invention is illustrated.

Referring now in detail to the drawing, a male member 1 is shown as one support element which is shaped as a conical pin having a rib 2 extending from the rear thereof which merges with crosspiece 3 running transversely thereto. When making the crown, this crosspiece can be anchored with the base of the crown, for example, soldered or molded therewith. In its lower portion, conical pin 1 is provided with a slot-like recess 4. An identical recess is provided on the opposite side of the pin. The recess may also comprise a groove extending almost over the total circumference of conically-shaped pin 1.

A female member 5 is fixedly mounted on the dental prosthesis or denture (not shown) as a support element, which consists of a conical bushing 7 with a longitudinal slot 6 which, in a positive locking manner, is pushed from above over the lower positioned pin 1.

In its lower portion, conical bushing 7 is provided with a radially extending protrusion or shoulder which has a centrally-disposed circumferential offset 9, which in the lower portion of bushing 7 merges on both sides into wall openings 10. A wire spring yoke 11 is shown which is slidable in the direction indicated by arrow 12 over offset 9 and beyond shoulder 8 and which comes to rest in the recess 9 of shoulder 8. The two free ends 13 and 14 project into wall openings 10 of the bushing, so that they yieldingly engage in recess 4 of the support element which is shaped as male member 1, when conical pin 1 and conical bushing 7 are telescopically pushed into each other.

At the same time, shoulder 8 serves to anchor bushing 7 to a dental prosthesis.

Thus, while only one embodiment of the present invention has been shown and described, it will be obvious that many changes and modifications may be made thereunto, without departing from the spirit and scope of the invention.

What is claimed is:

1. A support for a removable dental prosthesis on the remainder of the natural teeth, comprising:
    a male support element and a female support element, said male support element being securable to the base of a crown of a capped tooth of one's remaining natural teeth, and said female support member being securable to a dental prosthesis, said male support element and said female support element being configured for positive locking and telescopic displacement relative to one another and, in an end position thereof, mutual interengagement therebetween, said male support element comprising a vertically-disposed, generally conical pin having a recess, and said female support element comprising a vertically-disposed, generally conical bushing configured to encompass said pin which bushing is provided with an inwardly-protruding spring element removably mounted thereon which is disposed for bias engagement with said recess of said pin when said bushing is fully received on said pin.

2. The support according to claim 1, wherein said bushing has wall openings extending therethrough and said pin has correspondingly-positioned groove-like recesses and wherein said spring element comprises a wire spring yoke which engages the exterior surface of said bushing and which has resilient segments which project through said wall openings of said bushing, and engage said groove-like recesses of said pin when said bushing is fully received on said pin.

* * * * *